(12) United States Patent
Cirillo et al.

(10) Patent No.: US 6,503,220 B1
(45) Date of Patent: Jan. 7, 2003

(54) VAGINAL DOUCHING AND/OR ENTEROCLYSM DEVICE

(76) Inventors: Stefano Cirillo, Via Lobue, 2, 90010 Porticello (IT); Giuseppe Fucá, Via P. D'Asaro, 45, 90143 Palermo (IT)

( * ) Notice: Subject to any disclaimer, the term of this patent is extended or adjusted under 35 U.S.C. 154(b) by 0 days.

(21) Appl. No.: 09/462,132
(22) PCT Filed: Nov. 5, 1997
(86) PCT No.: PCT/EP97/06132
§ 371 (c)(1),
(2), (4) Date: Dec. 30, 1999
(87) PCT Pub. No.: WO98/20722
PCT Pub. Date: May 22, 1998

(30) Foreign Application Priority Data

Jul. 24, 1997 (IT) ......................... PA97A0017

(51) Int. Cl.⁷ ................................ A61M 3/02
(52) U.S. Cl. ....................................... 604/39
(58) Field of Search ............................ 604/36, 37, 39, 604/27, 279; 4/420.1, 443

(56) References Cited

U.S. PATENT DOCUMENTS

| 3,762,411 A | * | 10/1973 | Lloyd et al. ................. 415/116 |
| 4,622,704 A | * | 11/1986 | Chung ............................ 4/443 |
| 5,081,999 A | * | 1/1992 | Hemstreet |
| 5,097,540 A |   | 3/1992 | Lovitt |
| 5,669,394 A | * | 9/1997 | Bergey et al. ................. 604/37 |
| 5,746,721 A | * | 5/1998 | Pasch et al. ................. 604/153 |
| 5,864,895 A | * | 2/1999 | Ota et al. ....................... 4/443 |
| 5,941,851 A | * | 8/1999 | Coffey et al. ................ 604/131 |
| 6,059,754 A | * | 5/2000 | Pasch et al. ................. 604/152 |

FOREIGN PATENT DOCUMENTS

| FR | 2135144 | 12/1972 |
| GB | 2063674 | 6/1981 |
| WO | WO 00535 | 1/1986 |

* cited by examiner

Primary Examiner—Brian L. Casler
Assistant Examiner—Kevin C. Simmons
(74) Attorney, Agent, or Firm—Daniel O'Byrne

(57) ABSTRACT

A vaginal douching and/or enteroclysm device including a grip holder (26a) for being held by a user's hand, a cannula (36) connected to the grip holder (26a), a liquid container (24a) for containing liquids, and an electric pump (10) arranged for delivering fluid from the liquid holder (24a) to the cannula (36). The electric pump (10) is selectively activated by means of a switch (40) carried by the grip holder (26a) and actuatable when engaged by the user's hand. The electric pump (10) may be completely arranged inside the grip holder (26a), which may also contain a rechargeable battery (42) for operating the electric pump (10), and which may further support the liquid container (24a), while a base (44) is provided for removably supporting the grip holder (26a) such that the grip holder (26a) is completely removable from said base (44). Alternatively, the device may include a box (18) for containing the electric pump (10) and for supporting the liquid container (24) and the grip holder (26), and a bendable liquid delivery tube (32) interconnected between the grip holder (26) and the electric pump (10).

6 Claims, 4 Drawing Sheets

VAGINAL DOUCHING AND/OR ENTEROCLYSM DEVICE

TECHNICAL FIELD

The present invention relates to a vaginal douching and/or enteroclysm device with an electric pump.

BACKGROUND ART

The administration of drugs for topical local-regional use represents a great period of therapeutical importance in diverse illnesses which affect various anatomical regions. It is enough to remember, amongst all of them, the use of eye-washes in multiple ocular illnesses or of mouth-washes in certain pathological oro-pharyngeal processes.

In the same manner, there are numerous vaginal and rectal pathological conditions which require a local therapy respectively by douching and clysis.

In the gynaecological field the use of vaginal washes has, moreover, not only a therapeutic aim, but there also exists the considerable diffusion of this finalised practice also simply for personal hygiene.

In the proctological field, beyond the frequent recourse as much by the general population as in hospital environments to clyster for evacuational purposes, there is to be considered the notable incidence and prevalence in the western world of chronic intestinal inflammatory pathologies both specific and aspecific prevailingly rectal and sigmoidal localising which require a local therapy with specific antiinflammatory drugs.

The traditional systems used as much for vaginal douching as for enteroclysm employ containers connected to cannulas which allow the exit of the washing fluid only by gravity or by means of manual pressure.

These systems so assembled do not allow to regulate the nature and duration of the flow, such that in the major part of cases the douching does not reach the desired effectiveness, given that, for a correct cleansing and/or disinfection of the mucous membranes, the volume of solution which makes contact with the targeted mucosa and the time of the contact itself are equally important. This is equally valid in the gynaecological field and in the colon-proctological field.

Moreover, the common systems adopted for enteroclysm, in fact, show the same cited disadvantages for vaginal douching with the aggravating circumstance that a possible non-correct orientation of the douching cannula, for example erroneously placed in direct contact with the rectal wall, brings about the inevitable result of a scarce effectiveness of the clyster itself, with the consequence of an increase of the number of days of therapy and/or of the daily administration of the drug.

U.S. Pat. No. 5,097,540 discloses a self-contained hand-held bidet comprising a pistol configuration housing which contains a pump, and which carries controls and support for a retractable conduit with a nozzle end for spraying a stream of fluid from a reservoir mounted at one end of the housing. The retractable conduit and nozzle end are configured such that during use of the self-contained hand-held bidet, a stream of fluid is directed to the desired area but sufficiently away from the conduit and nozzle end for preventing soiling or contaminating material from the lavaged area from coming into contact with any part of the self-contained hand-held bidet, which is thus for external use.

WO-A-86 00535 discloses an irrigation device for personal hygiene comprising a torch-like case containing a battery electrical source for supplying, through a manually-operated external contol member mounted on the case, an electric motor fitted in the case which drives an centrifugal pump which is also fitted in the case and into which lead an intake pipe for an irrigating liquid and a delivery pipe connected to a tube having a shaped end with delivery nozzles for the liquid for insertion into the intimate part to be irrigated.

FR-A-2 135 144 discloses a portable compact electric douche for being held directly in a user's hand and having a nozzle element for insertion to a desired length within the vagina. The douche includes a casing containing an electric motor, battery, and switch for pumping douching fluid to the nozzle element, from a reservoir, in the form of a disposable sealed plastic bag, connected to the douche by a hose.

GB-A-2 063 674 discloses a portable medical treatment device including an injection nozzle configured to enter an ear cavity or wound. The device includes a pistol-shaped housing containing a pump, an electric motor for driving the pump, and a switch for the motor, operated by a trigger carried by the housing. A tube connects the injection nozzle, carried by the housing, to the pump, which is also connected to a cleaning fluid reservoir by means of a flexible tube extending away from the housing.

It is a general object of the present invention to provide improvements in vaginal douching and/or enteroclysm devices.

DISCLOSURE OF THE INVENTION

In accordance with one preferred aspect of the present invention, there is provided a variable pressure and controlled electric pump for vaginal and/or rectal douching with natural and/or medicated liquids for local use, which allows to obtain, with respect to conventional methods, a more effective and controlled douching, favouring an improved hospital or domestic utilisation with the use of single-use endovaginal or rectal cannulas.

The vaginal douching and/or enteroclysm device of the invention in a preferred embodiment comprises an electric pump with a velocity switch lodged in a plastic material container, a liquid container, replaceable with ready medicated containers, a flexible tube for liquid passage, through the pump, from the container to the cannula, ergonomic grip holder with open and close command for the passage of liquid, and the vaginal and/or rectal cannula.

The present invention offers the following significant advantages with respect to the traditional systems:

a) increased convenience of use, for the possibility to adequately direct the flow of douching fluid due to the anatomicalness of the grip holder of the douching cannula and to the presence on the same of the on/off control, which allows the patient to focus his own attention exclusively on the correct positioning of the cannula rather than on the injection of the therapeutic solution which, in systems in use up to now, require the use of both hands in order to exert the correct pressure adapted to its exit; for the preventive regulation of the velocity of the douching flow in relation to the anatomical seat and to the pathology to treat; for the absolute management autonomy of the system on the part of the user;

b) greater therapeutical effectiveness, in that the constancy of the flow offers the possibility of an increased duration of the douching with an equal volume of solution administered, which translates in a more prolonged contact of the mucosa with the drug and, consequently, in an increased therapeutical effectiveness;

c) optimal cost/benefit ratio, in that the lesser cost of each single therapeutic cycle due to the improved utilisation of the drug permits the rapid recovery of the amount spent on the acquisition of the system:, d) hygienic security, for the impossibility of reflow of the solution in the context of the washing system by the unidirectionality of the flow which saves the solution container from possible external contaminations. This is of particular importance in case of prolonged cyclic therapeutics for the convenience of carrying out a single loading of the reservoir, usable also in successive days. Moreover, the availability of single-use reservoirs obtains an easy utilisation also in hospital environments where the system may be employed on more patients with the simple substitution of the douching cannula and of the reservoir, with a consequent notable reduction of the technical times on the part of the nursing personnel.

BRIEF DESCRIPTION OF DRAWINGS

The particular technical characteristics and advantages of the invention will become apparent to a skilled person in the art from the following detailed description of some preferred but not exclusive embodiments of a vaginal douching and/or enteroclysm device according to the invention, described hereinafter and illustrated in the accompanying drawings only by way of non-limitative example in which.

BEST MODES FOR CARRYING OUT THE INVENTION

Figure 1:
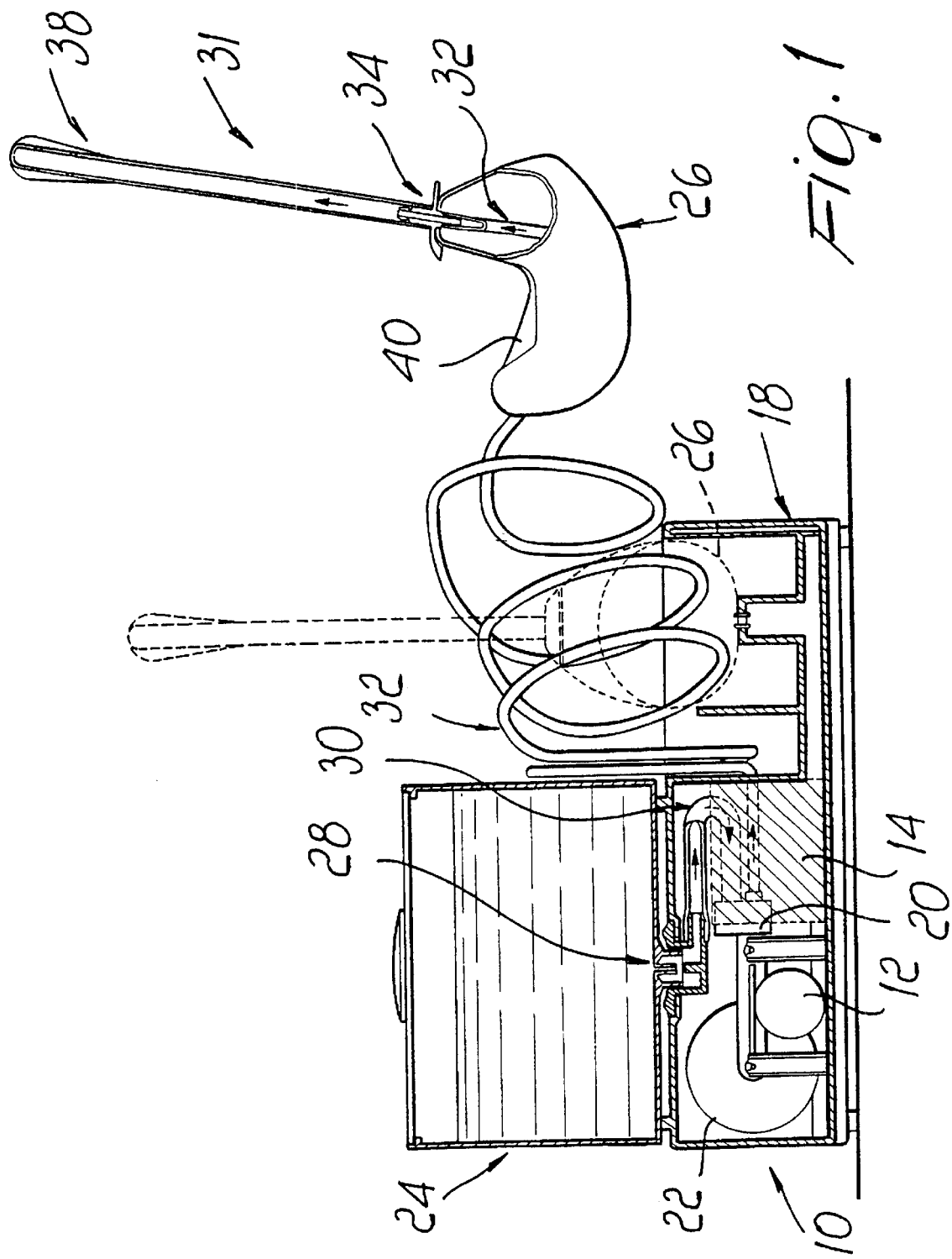
FIG. 1 is a partially sectional side elevational view of a first embodiment of the device according to the invention.

In the drawing Figures, like reference numerals indicate like parts.

The vaginal douching and/or enteroclysm device according to the present invention may be made in material of a plastic nature or in other suitable materials, in compliance with the hygienic-sanitary criteria and norms, and such device has an electrical operation. The device may be utilised in a hospital environment or for personal use in a domestic environment.

The vaginal douching and/or enteroclysm device comprises an electrical pump 10 through which it is possible to dose the liquid flow, improving and controlling personal hygiene.

A switch 40, which will be described more in detail hereinafter, is provided for selectively turning electrical pump 10 on and off.

Figure 4:
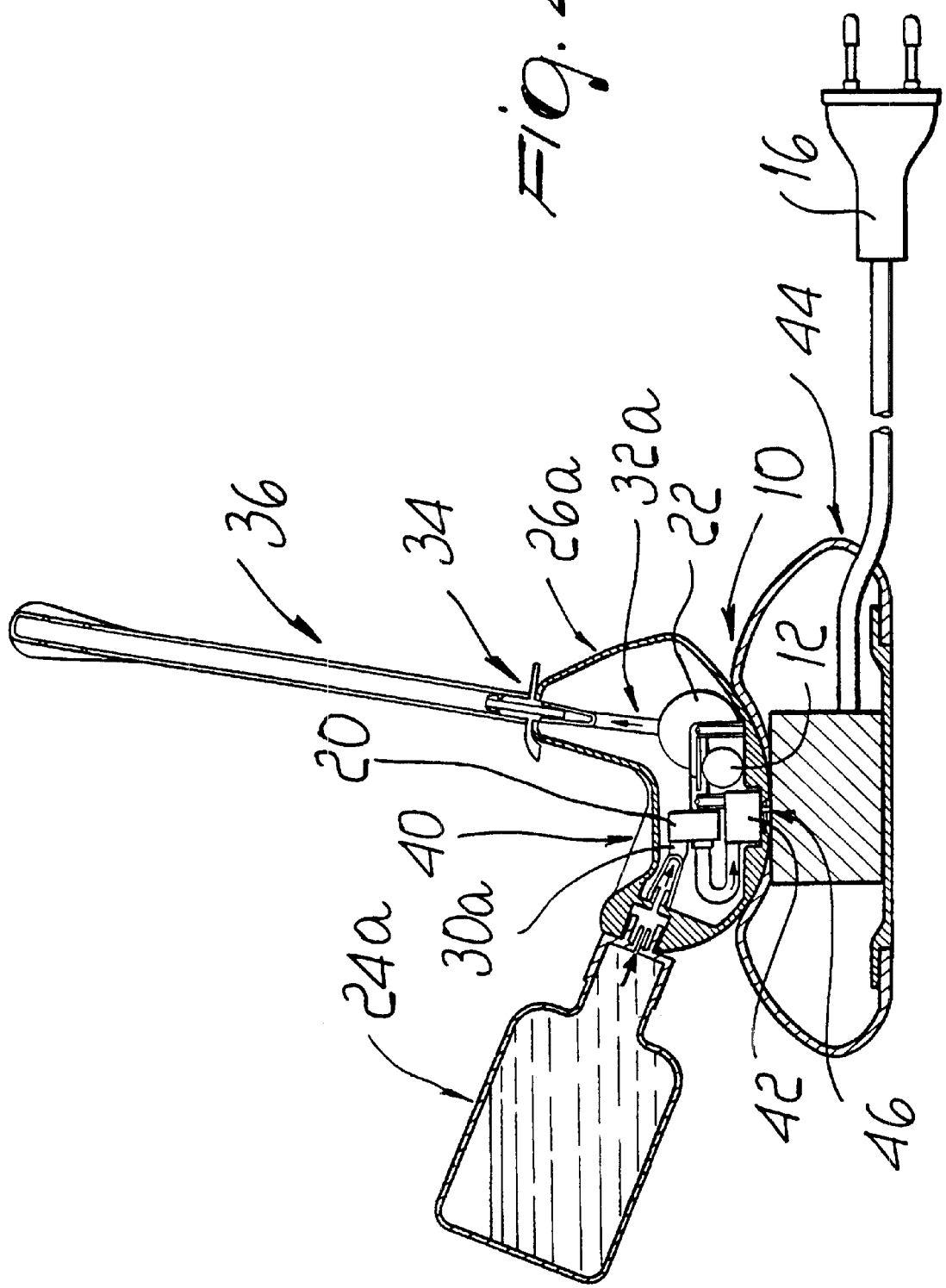
FIG. 4 is a partially sectional side elevational view of a second embodiment of the device according to the invention.

Electrical pump is furnished with an electric motor 12, preferably of a 12 volt type and connected to a current transformer 14. The entire system may be connected to a normal 220 volt current socket, for example by means of an electric plug 16 as seen in FIG. 4. The system may function as well with a battery, in a manner to allow for detachment of the device current socket during its use.

For the utilisation in particular in a hospital environment the device (see FIGS. 1 and 2) is provided with a box 18 which holds electric motor 12 and transformer 14, and which further holds the other elements of pump 10 including a pumping mechanism 20 and a speed variator 22 for motor 12. Box 18 further constitutes a support for: a liquid tank 24 for containing the liquids to be delivered by the device; and for an anatomic grip holder 26 shaped so as to be easily and effectively grasped by a human hand.

Liquid tank 24, preferably having a prismatic shape with a capacity of 500 milliliters, is connected through a coupling insertion valve 28, located at the base of tank 24, to a fluid conduction tube 30 which allows the liquid to flow towards pumping mechanism 20 of pump 10 and from here, by means of a delivery tube 32, the liquid is conducted to anatomic grip holder 26. Deliver tube 32 is bendable and elongated to allow grip holder 26 to be removed from its support position (FIG. 2 and dashed lines in FIG. 1) on box 24 and moved distally away from box 24 into its use position (FIG. 1). Deliver tube 32 also is arranged to extend inside grip holder 26 (FIG. 1) and be connected to a coupling 34 which connects an internally hollow cannula 36 to grip holder 26, in a manner to permit liquid to flow from delivery tube 32 inside cannula 36 and out through a series of holes 38 provided at the tip of cannula 36.

Grip holder 26 is designed for an ergonomic use and is conceived for a permitting a convenient selective actuation of electric pump 10 to regulate the flow of liquid described above by means of switch 40 carried by grip holder 26, while one is free to manoeuvre cannula 36 lodged in grip holder 26.

Switch 40 may comprise a spring biased button carried by grip holder 26 such that when grip holder 26 is held by a user's hand the button is engaged by the user's hand to turn on electric pump 10, and such that the button is biased outwardly on grip holder 26 when grip holder 26 is not held by a user's hand to turn off electric pump 10. In the preferred embodiment switch 40 in the form of a spring biased button is for being engaged by a user's palm.

Figure 6:
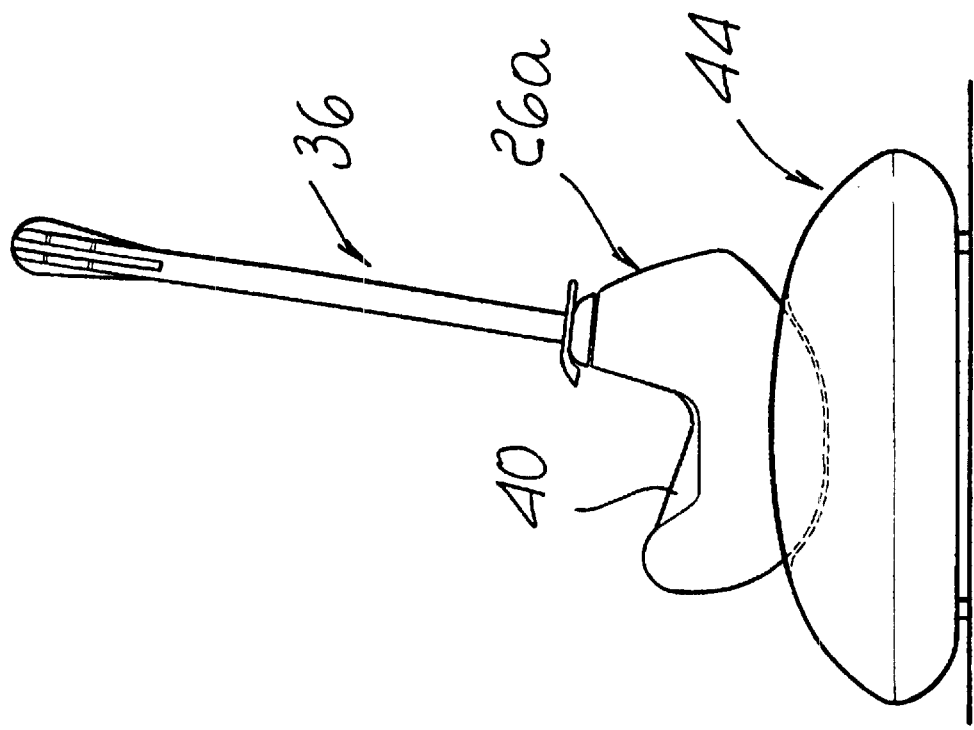
FIG. 6 is a side elevational view of the device of FIG. 4.
Figure 5:
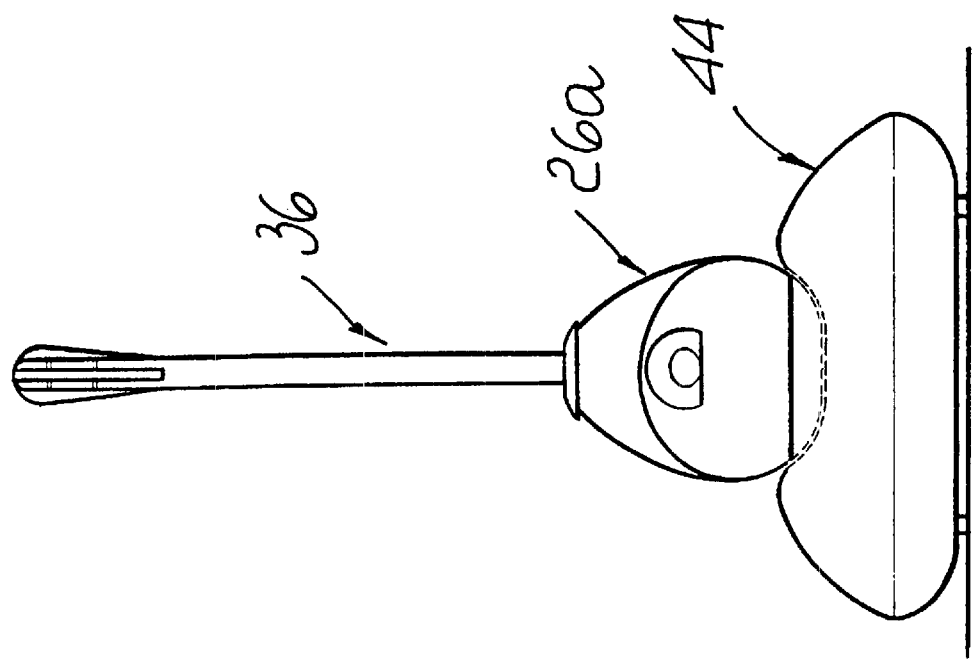
FIG. 5 is a front elevational view of the device of FIG. 4.

In another embodiment of the device according to the invention (FIGS. 4–6) which is particularly useful for personal domestic use, there is provided a tank 24a for containing the liquid which is preferably a use-and-throw-away 100–150 milliliter container inserted directly in anatomic grip holder 26a for fluid connection to pump 10 which is contained completely inside grip holder 26a. Fluid conduction tube 30a and delivery tube 32a have correspondingly reduced dimensions also for being completely contained inside grip holder 26a. Grip holder 26a carries switch 40 and coupling 34 for cannula 36 in a manner similar to the previously described embodiment.

For autonomous handing of the device according to the invention, a battery 42 for powering pump 10 is arranged inside grip holder 26a. A resting base 44 is provided for supporting grip holder 26a such that grip holder 26a is completely removable from base 44. Battery 42 may be rechargeable, provided for example by means of charging contact pins 46 located in the upper part of base 44. Pins 46 are electrically connected with electrical plug 16 and are arranged for being electrically connected with battery 42 when grip holder 26a is positioned on resting base 44, for charging battery 42. Base 44 internally contains current transformer 14. During the utilisation phase grip holder 26a is completely detached from base 44 and, therefore, from the connection to the electrical mains.

Figure 2:
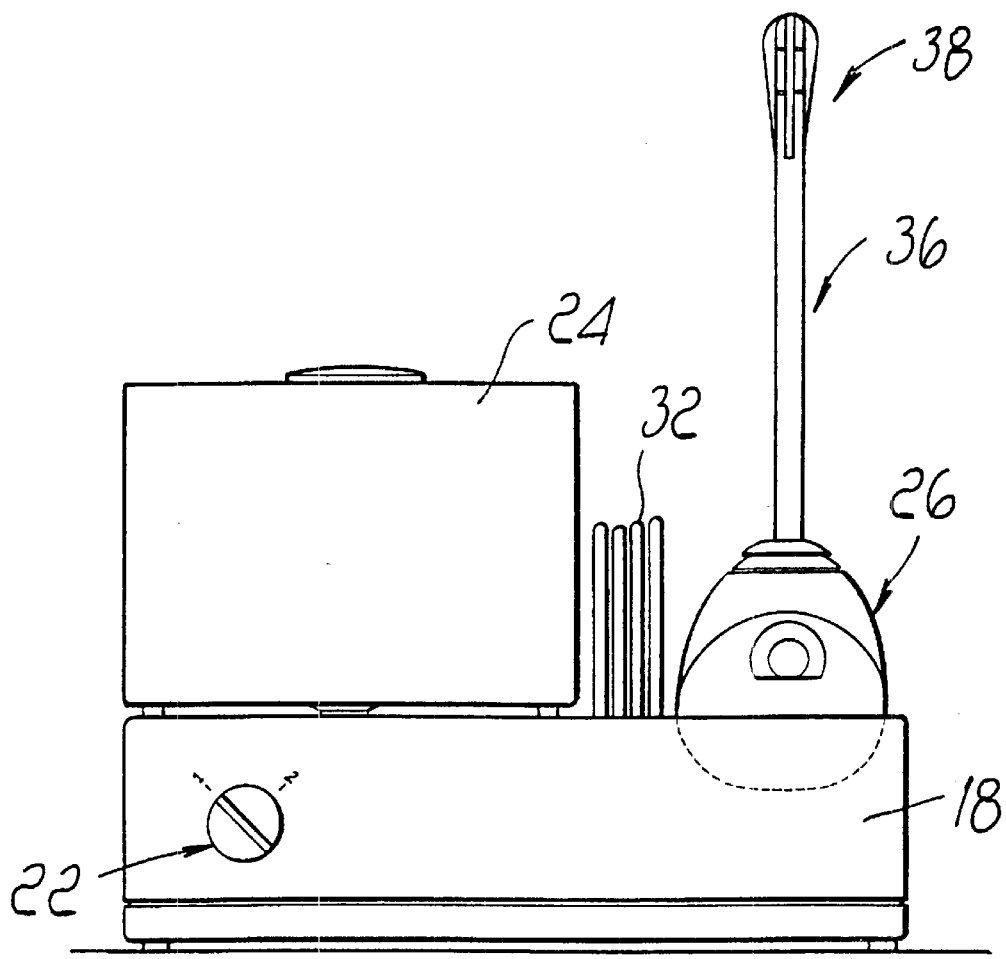
FIG. 2 is a side elevational view of the device of FIG. 2.

Grip holder 26 of the embodiment of FIGS. 1 and 2 may similarly contain a battery which is electrically rechargeable by means of charging contact pins 46a supported by box 18.

Figure 3A:
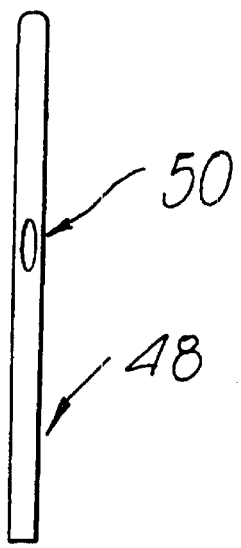
FIGS. 3a and 3b are perspective view of cannulas according to the invention.
Figure 3B:
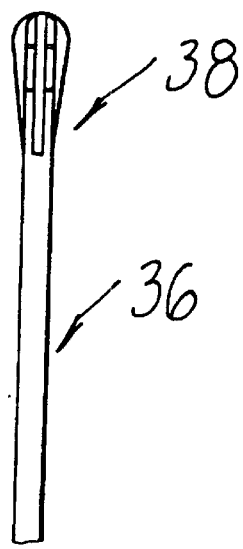

Cannula 36 is in particular a vaginal cannula provided at its end with a series of small holes 38 for the exit of the liquid (FIG. 3*b*). The device according to the invention may also employ a rectal cannula 48 provided with one hole 50 for the exit of the liquid (FIG. 3*a*). Cannulas 36 and 48 may be easily and selectively attached/detached to coupling 34.

What is claimed is:

1. A vaginal douching and/or enteroclysm device comprising:
   a grip holder for being held by a user's hand;
   an internal-use endovaginal or rectal connected to said grip holder;
   a resting base or box configured for removably supporting said grip holder above a support surface upon which said resting base or box is supported during a non-use rest configuration of the device;
   a liquid container for containing liquids and carried by said grip holder; and
   an electric pump arranged inside said grip holder and for delivering fluid from said liquid container to said cannula;
   a battery connected to said electric pump and arranged inside said grip holder; and
   means for recharging said battery operable when said grip holder is supported by said base during said non-use rest configuration of said device.

2. The device of claim 1 wherein said electric pump comprises;
   pumping mechanism, and
   electric motor,
   said pumping device being connected to said electric motor for being driven by said electric motor.

3. The device of claim 1, further comprising a switch carried by said grip holder and connected to said electric pump wherein said electric pump is selectively activated by means of said switch.

4. The device of claim 3 wherein said switch comprises a spring biased button carried by said grip holder in a position on said grip holder such that when said grip holder is held by a user's hand said button is engageable by the user's hand to turn on said electric pump, and such that said button is biased outwardly on said grip holder in a non-engaged position of said button to turn off said electric pump.

5. The device of claim 4 in said button is arranged in said position said grip holder for being engageable by a user's palm.

6. A vaginal douching and/or enteroclysm device comprising:
   a grip holder or being held by a user's hand;
   an internal-use endovaginal or rectal cannula connected to said grip holder;
   a resting base or box configured for removably supporting said grip holder above a support surface upon which said resting base or box is supported during a non-use rest configuration of the device;
   a liquid container for containing liquids and carried by said grip holder or by said box; and
   an electric pump carried by said grip holder or by said box and arranged for delivering fluid from said liquid container to said cannula said electric pump comprising a pumping mechanism, and an electric motor said pumping mechanism being connected to said electric motor for being driven by said electric motor;
   said box carrying said electric pump and supporting said liquid container, and the device further comprising:
      a bendable liquid delivery tube interconnected between said grip holder and said electric pump;
      a battery arranged inside said grip holder; and
      means for recharging said battery operable when said grip holder is supported by said box during said non-use rest configuration of the device.

* * * * *